United States Patent
Zhang

(10) Patent No.: US 8,220,340 B2
(45) Date of Patent: Jul. 17, 2012

(54) PERMANENT DEFORMATION MEASUREMENT APPARATUS FOR ELASTIC MEMBER

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 273 days.

(21) Appl. No.: 12/684,125

(22) Filed: Jan. 8, 2010

(65) Prior Publication Data

US 2011/0036184 A1    Feb. 17, 2011

(30) Foreign Application Priority Data

Aug. 13, 2009   (CN) .......................... 2009 1 0305570

(51) Int. Cl.
   *G01N 3/02*         (2006.01)
(52) U.S. Cl. ..................................... 73/856; 73/862.621
(58) Field of Classification Search ................... 73/849, 73/851, 856, 862.621
   See application file for complete search history.

(56) References Cited

U.S. PATENT DOCUMENTS

| | | | | |
|---|---|---|---|---|
| 4,489,586 A | * | 12/1984 | Hess | 72/389.3 |
| 4,747,208 A | * | 5/1988 | Sbalchiero et al. | 29/726 |
| 4,761,979 A | * | 8/1988 | Kawaguchi et al. | 72/16.2 |
| 5,050,420 A | * | 9/1991 | Liu | 72/391.4 |
| 5,460,452 A | * | 10/1995 | Hara | 384/45 |
| 7,007,530 B2 | * | 3/2006 | Koyama et al. | 72/31.1 |

* cited by examiner

*Primary Examiner* — Max Noori
(74) *Attorney, Agent, or Firm* — Altis Law Group, Inc.

(57) ABSTRACT

A permanent deformation measurement apparatus includes a worktable and a measuring device. The worktable includes a supporting surface for supporting an elastic member to be measured. The measuring device includes a base, contact member, an operating member, and a measuring member. The base is fixed on the supporting surface, and defines a guide hole substantially perpendicular to the supporting surface of the worktable. The contact member includes a push rod slidable along the guide hole to contact the elastic member. The operating member is configured for moving the push rod. The measuring member is configured for measuring a position of the push rod when the push rod is in contact with the elastic member.

14 Claims, 2 Drawing Sheets

PERMANENT DEFORMATION MEASUREMENT APPARATUS FOR ELASTIC MEMBER

BACKGROUND

1. Technical Field

The present disclosure relates to measurement apparatuses and, particularly, to a permanent deformation measurement apparatus for an elastic member.

2. Description of Related Art

As is known, elasticity is a property of elastic members, such as elastic sheets, which, following deformation, automatically recover the relaxed, pre-deformation configuration when deforming forces thereon are removed. An ideal elastic member can automatically recover its normal configuration completely after the deforming forces are removed. However, the majority of elastic members cannot completely recover normal configuration, with some degree of permanent deformation relative to original configuration becoming inherent with use. The amount of permanent deformation of the elastic member following a determined number of deformative events determines the overall useful elasticity and the life of the elastic member.

What is needed, therefore, is a measurement apparatus determining elasticity of an elastic member.

BRIEF DESCRIPTION OF THE DRAWINGS

Many aspects of the present permanent deformation measurement apparatus for an elastic member can be better understood with reference to the accompanying drawings. The components in the drawings are not necessarily drawn to scale, the emphasis instead being placed upon clearly illustrating the principle of the present permanent deformation measurement apparatus for an elastic member. In the drawings, all the views are schematic.

DETAILED DESCRIPTION

Embodiments of the present disclosure will now be described in detail below, with reference to the accompanying drawings.

Figure 1:
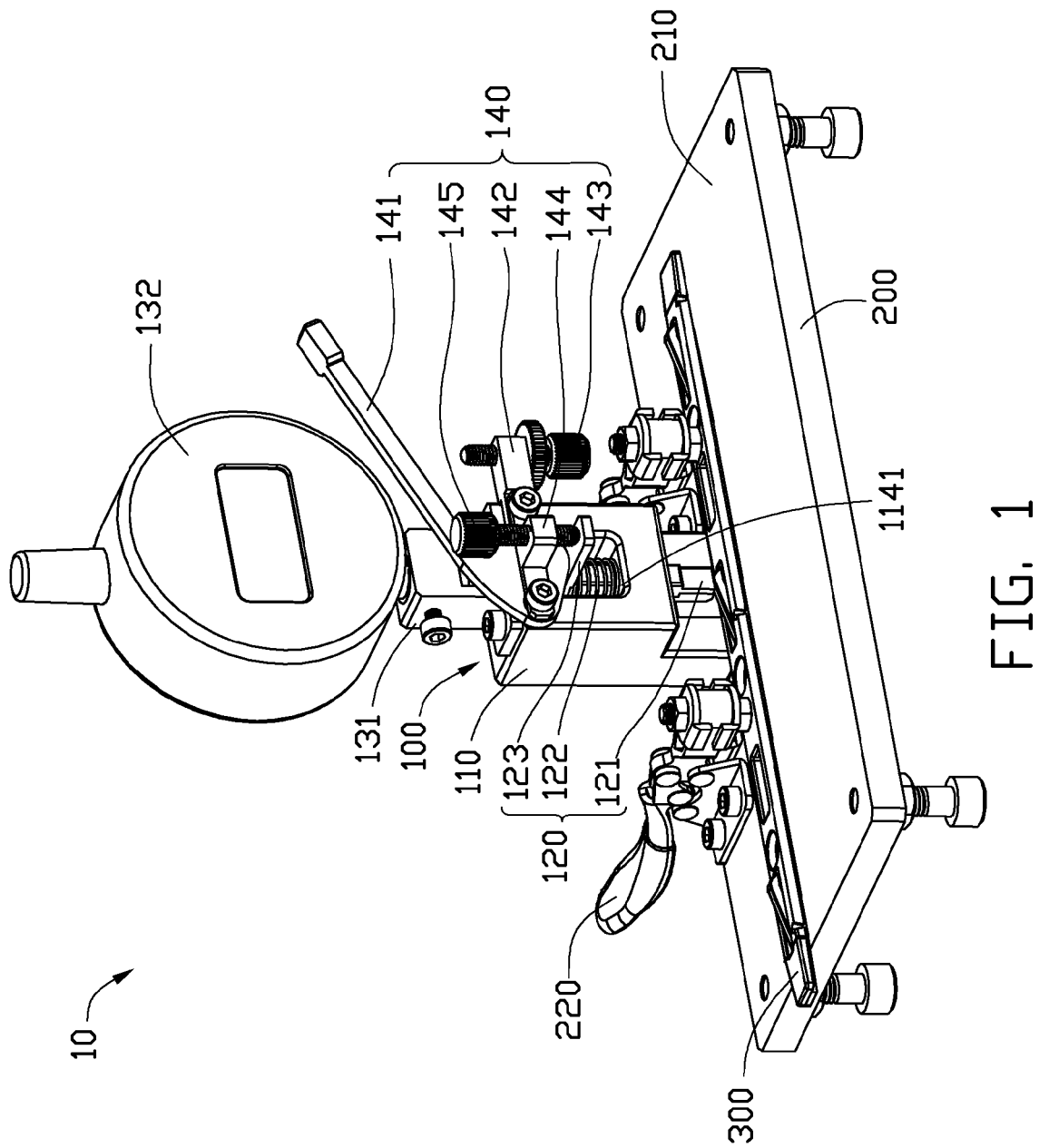
FIG. 1 is an assembled, isometric view of a permanent deformation measurement apparatus for an elastic member according to an exemplary embodiment.
Figure 2:
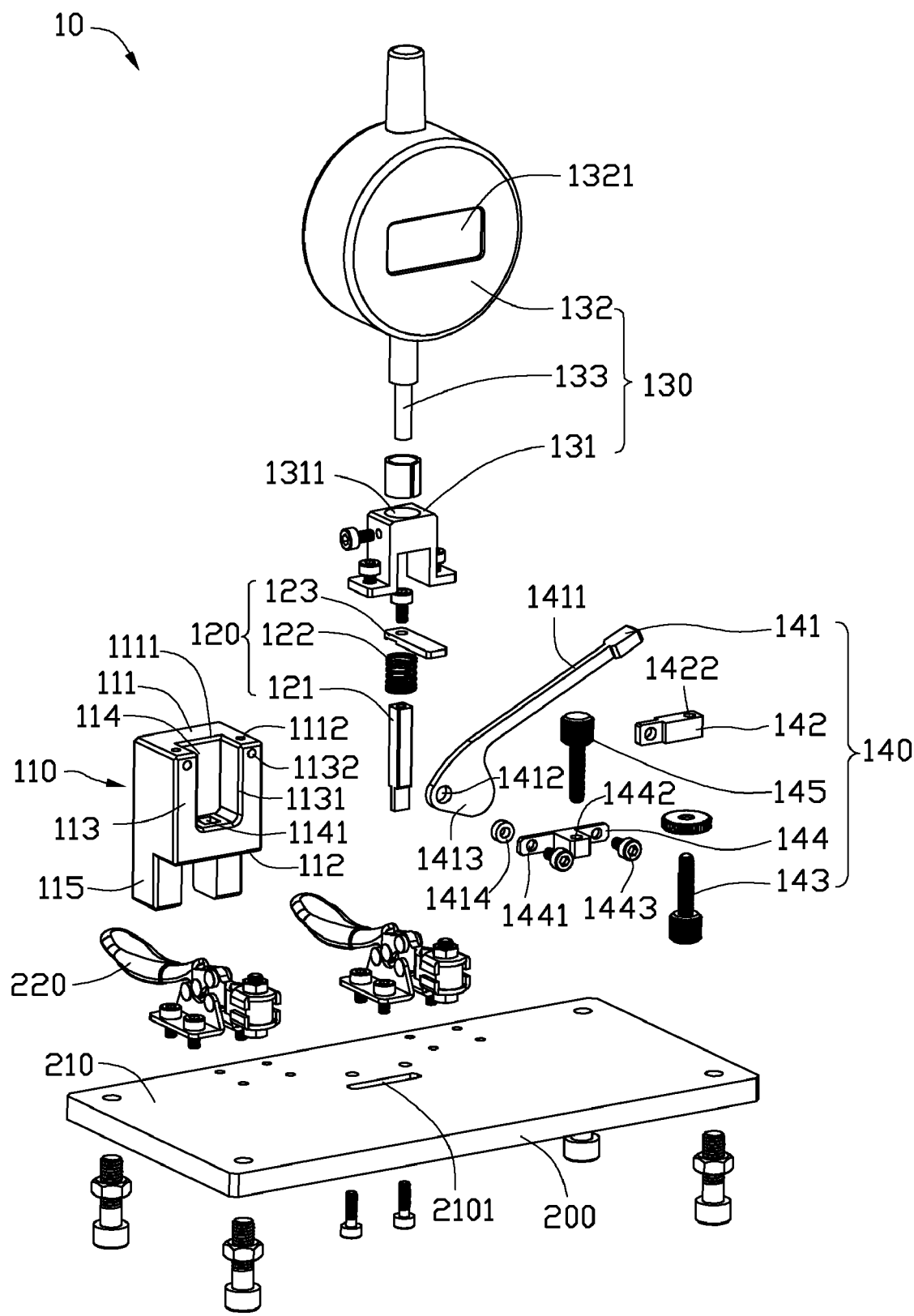
FIG. 2 is an exploded, isometric view of the permanent deformation measurement apparatus of FIG. 1.

Referring to FIGS. 1 and 2, a permanent deformation measurement apparatus 10 for testing an elastic member 300, according to an exemplary embodiment, is shown. In the present embodiment, the elastic member 300 is an elastic sheet. The permanent deformation measurement apparatus 10 includes a worktable 200 and a measuring device 100.

The worktable 200 includes a supporting surface 210 and two clamping devices 220 for fixing the elastic member 300 on the supporting surface 210 for measurement. In the present embodiment, the supporting surface 210 defines a receiving slot 2101 for receiving the elastic sheet when being bent.

The measuring device 100 includes a base 110, a contact member 120, a measuring member 130, and an operating member 140.

The base 110 includes a top surface 111, a bottom surface 112, and a side surface 113 connecting the top surface 111 to the bottom surface 112. The base 110 also includes two feet 115 extending towards the supporting surface 210 from the bottom surface 112 for connecting to the supporting surface 210 to support the base 110. The base 110 defines a receiving space 114 with a first opening 1111 on the top surface 111 and a second opening 1131 on the side surface 113, and a guide hole 1141 communicating with the receiving space 114. The guide hole 1141 runs through the bottom surface 112 of the base 110 and the bottom wall of the receiving space 114, and is substantially aligned with the receiving slot 2101. The axis of the guide hole 1141 is substantially perpendicular to the supporting surface 210 of the worktable 200. The base 110 further defines two threaded holes 1112 on the top surface 111 and two threaded holes 1132 on the side surface 113.

The contact member 120 includes a push rod 121, a spring 122, and a blocking board 123 fixed to an end of the push rod 121 away from the supporting surface 210. The push rod 121 is received in the guide hole 1141 and slidable along the guide hole 1141. The spring 122 sleeves the on push rod 121, and has one end resisting the bottom wall of the receiving space 114 and the other end resisting the blocking board 123. The blocking board 123 has a part thereof extending out of the receiving space 14 from the second opening 1131 to engage the operating member 140.

The operating member 140 includes a lever 141, a connecting portion 142, a threaded limiting fastener 143, a first supporting portion 144, and an threaded adjustment fastener 145.

The first supporting portion 144 defines two threaded holes 1441 corresponding to the two threaded holes 1132 of the base 110, and is fixed to the side surface 113 of the base 110 by two threaded fasteners 1443. The first supporting portion 144 further defines a threaded hole 1442 for receiving the threaded adjustment fastener 145. The axis of the threaded hole 1442 is substantially perpendicular to the supporting surface 210. The threaded adjustment fastener 145 resists the blocking board 123.

The lever 141 includes a handle 1411 and a contact portion 1413. The lever 141 defines an axle hole 1412 with an axle bushing 1414 received therein. The axle bushing 1414 is fixed between the first supporting portion 144 and the side surface 113 of the base 110. The contact portion 1413 contacts the blocking board 123 of the contact member 120 to move the push rod 121 by applying a force on the handle 1411.

The connecting portion 142 is fixed to the first supporting portion 144, and defines a threaded hole 1422 for receiving the threaded limiting fastener 143. The threaded limiting fastener 143 limits the rotation angle of the handle 1411 of the lever 141, therefore, the moving distance of the push rod 121 can be limited accordingly.

The measuring member 130 includes a second supporting portion 131, a housing 132 and a ruler 133. The second supporting portion 131 is fixed to the top surface 111 of the base 110. The second supporting portion 131 defines a through hole 1311 communicating with the receiving space 114. The ruler 133 is received in the housing 132, with one end connecting to the blocking board 123 through the through hole 1311. The ruler 133 is movable together with the push rod 121. The housing 132 defines a view window 1321 displaying the value of the ruler 133.

In order to measure permanent deformation of the elastic member 300, the threaded adjustment fastener 145 is adjusted such that push rod 121 makes slight contact with the elastic member 300 and records a first value of the ruler 133 at that time. The elastic member 300 is deformed a predetermined number of times by moving the push rod 121. The threaded adjustment fastener 145 is impelled to contact the push rod 121 slightly with elastic member 300 again and a second value is displayed on the ruler 133. As a result of permanent deformation, the second value will be different from the first value, and the amount of the permanent deformation of the elastic member can be calculated by the first value and the second value.

While certain embodiments have been described and exemplified above, various other embodiments will be apparent to those skilled in the art from the foregoing disclosure. The invention is not limited to the particular embodiments described and exemplified, and the embodiments are capable of considerable variation and modification without departure from the scope and spirit of the appended claims.

What is claimed is:

1. A permanent deformation measurement apparatus comprising:
    a worktable comprising a supporting surface for supporting an elastic member to be measured; and
    a measuring device comprising:
        a base fixed on the supporting surface, the base defining a guide hole substantially perpendicular to the supporting surface of the worktable;
        a contact member comprising a push rod slidable along the guide hole to contact the elastic member;
        an operating member for moving the push rod, the operating member comprising a threaded adjustment fastener resisting the end of the push rod away from the supporting surface; and
        a measuring member for measuring a position of the push rod when the push rod is in contact with the elastic member.

2. The permanent deformation measurement apparatus as claimed in claim 1, wherein the worktable further comprises a clamping device for fixing the elastic member on the supporting surface; and the measuring member comprises a ruler connected to an end of the push rod away from the worktable for measuring a position of the push rod when the push rod is in contact with the elastic member.

3. The permanent deformation measurement apparatus as claimed in claim 1, wherein the supporting surface defines a receiving slot substantially aligned with the guide hole.

4. The permanent deformation measurement apparatus as claimed in claim 1, wherein the operating member further comprises a lever comprising a handle and a contact portion, the contact portion impelling the push rod by applying a force on the handle.

5. The permanent deformation measurement apparatus as claimed in claim 2, wherein the measuring member further comprises a housing for receiving the ruler, the housing defining a view window displaying the value of the ruler.

6. The permanent deformation measurement apparatus as claimed in claim 1, wherein the base comprises a bottom surface facing the supporting surface, a top surface opposite to the bottom surface, and a side surface connecting the top surface to the bottom surface.

7. The permanent deformation measurement apparatus as claimed in claim 6, wherein the base further comprises two feet extending towards the supporting surface from the bottom surface for connecting to the supporting surface to support the base.

8. The permanent deformation measurement apparatus as claimed in claim 6, wherein the base defines a receiving space communicated with the guide hole, and the receiving space has a first opening on the top surface and a second opening on the side surface.

9. The permanent deformation measurement apparatus as claimed in claim 8, wherein the contact member further comprises a spring and a blocking board, the blocking board being fixed to an end of the push rod away from the supporting surface, and the spring sleeving the push rod with one end resisting the bottom wall of the receiving space and the other end resisting the blocking board.

10. The permanent deformation measurement apparatus as claimed in claim 9, wherein the operating member further comprises a lever and a supporting portion, the supporting portion is fixed to the side surface of the base, the lever is rotatable relative to the supporting portion, and comprises a handle and a contact portion, and the contact portion is used for pressing the push rod to move the push rod by applying a force on the handle.

11. The permanent deformation measurement apparatus as claimed in claim 10, wherein the supporting portion defines a threaded hole for receiving the threaded adjustment fastener, the axis of the threaded hole of the supporting portion is substantially perpendicular to the supporting surface, and the threaded adjustment fastener resists the blocking board.

12. The permanent deformation measurement apparatus as claimed in claim 11, wherein the operating member further comprises a connecting portion and a threaded limiting fastener, the connecting portion is connected to the supporting portion and defines a threaded hole for receiving the threaded limiting fastener, and the threaded limiting fastener restricts the rotation angle of the handle of the lever.

13. A permanent deformation measurement apparatus comprising:
    a worktable comprising a supporting surface for supporting an elastic member to be measured; and
    a measuring device comprising:
        a base fixed on the supporting surface, the base comprising a bottom surface facing the supporting surface, a top surface opposite to the bottom surface, a side surface connecting the top surface to the bottom surface, and two feet extending towards the supporting surface from the bottom surface of the base for connecting to the supporting surface to support the base, and the base defining a guide hole substantially perpendicular to the supporting surface of the worktable;
        a contact member comprising a push rod slidable along the guide hole to contact the elastic member;
        an operating member for moving the push rod; and
        a measuring member for measuring a position of the push rod when the push rod is in contact with the elastic member.

14. A permanent deformation measurement apparatus comprising:
    a worktable comprising a supporting surface for supporting an elastic member to be measured; and
    a measuring device comprising:
        a base fixed on the supporting surface, the base comprising a bottom surface facing the supporting surface, a top surface opposite to the bottom surface, and a side surface connecting the top surface to the bottom surface, the base defining a guide hole substantially perpendicular to the supporting surface of the worktable, and a receiving space communicated with the guide hole, the receiving space having a first opening on the top surface and a second opening on the side surface;
        a contact member comprising a push rod slidable along the guide hole to contact the elastic member, a spring, and a blocking board, the blocking board being fixed to an end of the push rod away from the supporting surface, and the spring sleeving the push rod with one end resisting the bottom wall of the receiving space and the other end resisting the blocking board;
        an operating member for moving the push rod, the operating member comprising a lever, a supporting portion, and a threaded adjustment fastener, the supporting portion being fixed to the side surface of the base, the lever being rotatable relative to the supporting portion, the lever comprising a handle and a contact portion, the contact portion being used for pressing the push rod to move the push rod by applying a force on the handle, the supporting portion defining a threaded hole for receiving the threaded adjustment fastener, the axis of the threaded hole of the supporting portion being substantially perpendicular to the supporting surface, and the threaded adjustment fastener resisting the blocking board; and a measuring member for measuring a position of the push rod when the push rod is in contact with the elastic member.

* * * * *